(12) United States Patent
Hirai

(10) Patent No.: US 6,782,077 B2
(45) Date of Patent: Aug. 24, 2004

(54) IMAGING APPARATUS, IMAGING SYSTEM, CONTROL METHOD OF IMAGING APPARATUS, AND STORAGE MEDIUM WITH TIMING CONTROL FUNCTIONALITY

(75) Inventor: Akira Hirai, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 09/820,575

(22) Filed: Mar. 29, 2001

(65) Prior Publication Data

US 2001/0041832 A1 Nov. 15, 2001

(30) Foreign Application Priority Data

Mar. 31, 2000 (JP) .................................. 2000-096455

(51) Int. Cl.$^7$ ................................................ G21K 1/00
(52) U.S. Cl. ...................... 378/155; 378/154; 378/98.8
(58) Field of Search .......................... 378/4, 8, 96, 97, 378/98, 98.8, 114, 154, 155; 250/370.01, 370.08, 370.09

(56) References Cited

U.S. PATENT DOCUMENTS

| | | | |
|---|---|---|---|
| 4,810,881 A | 3/1989 | Berger et al. | .......... 250/370.01 |
| 5,132,539 A | 7/1992 | Kwasnick et al. | .......... 250/361 |
| 5,379,335 A | * 1/1995 | Griesmer et al. | ............ 378/155 |
| 5,396,072 A | 3/1995 | Schiebel et al. | ........ 250/370.09 |
| 5,418,377 A | 5/1995 | Tran et al. | ................ 250/483.1 |
| 5,381,014 A | 6/1997 | Jeromin et al. | ........ 250/370.09 |
| 6,304,632 B1 | 10/2001 | Rick et al. | .................. 378/155 |
| 6,330,303 B1 | * 12/2001 | Yamane et al. | ............ 378/98.8 |
| 6,510,202 B2 | * 1/2003 | Tamura et al. | .............. 378/155 |
| 2002/0001366 A1 | * 1/2002 | Tamura et al. | .............. 378/155 |

\* cited by examiner

*Primary Examiner*—Craig E. Church
*Assistant Examiner*—Therese Barber
(74) *Attorney, Agent, or Firm*—Morgan & Finnegan, LLP

(57) ABSTRACT

The object of the present invention is to provide a satisfactory image at a desired imaging timing by implementing grid movement control according to the time response characteristics of the radiation generation function and a decrease in time delay from an imaging request to actual irradiation. In order to achieve this object, a control device controls the actual irradiation instruction timing for an irradiation device on the basis of a pre-irradiation delay time as a time between an instruction and irradiation of actual irradiation of the irradiation device.

29 Claims, 6 Drawing Sheets

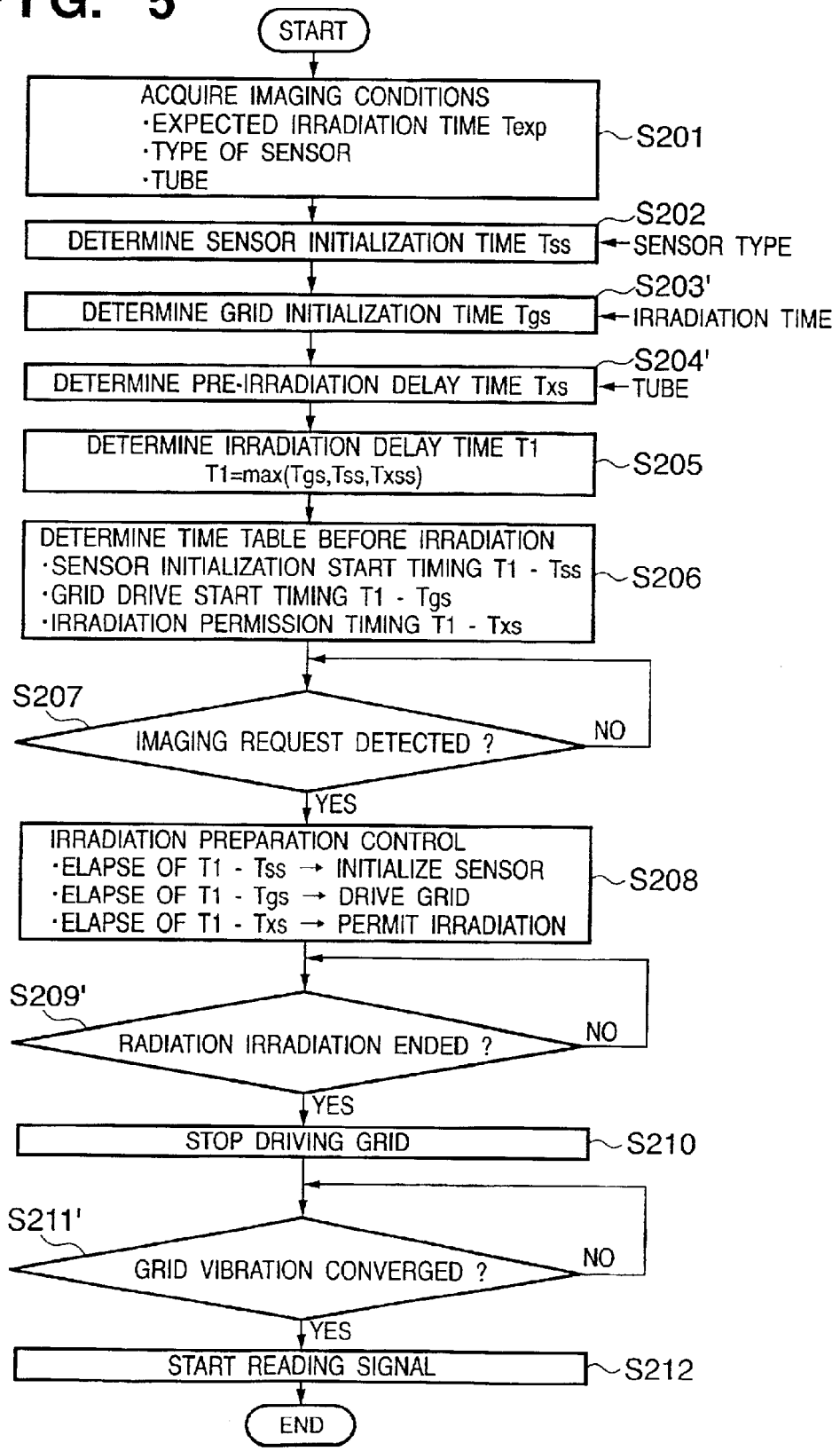

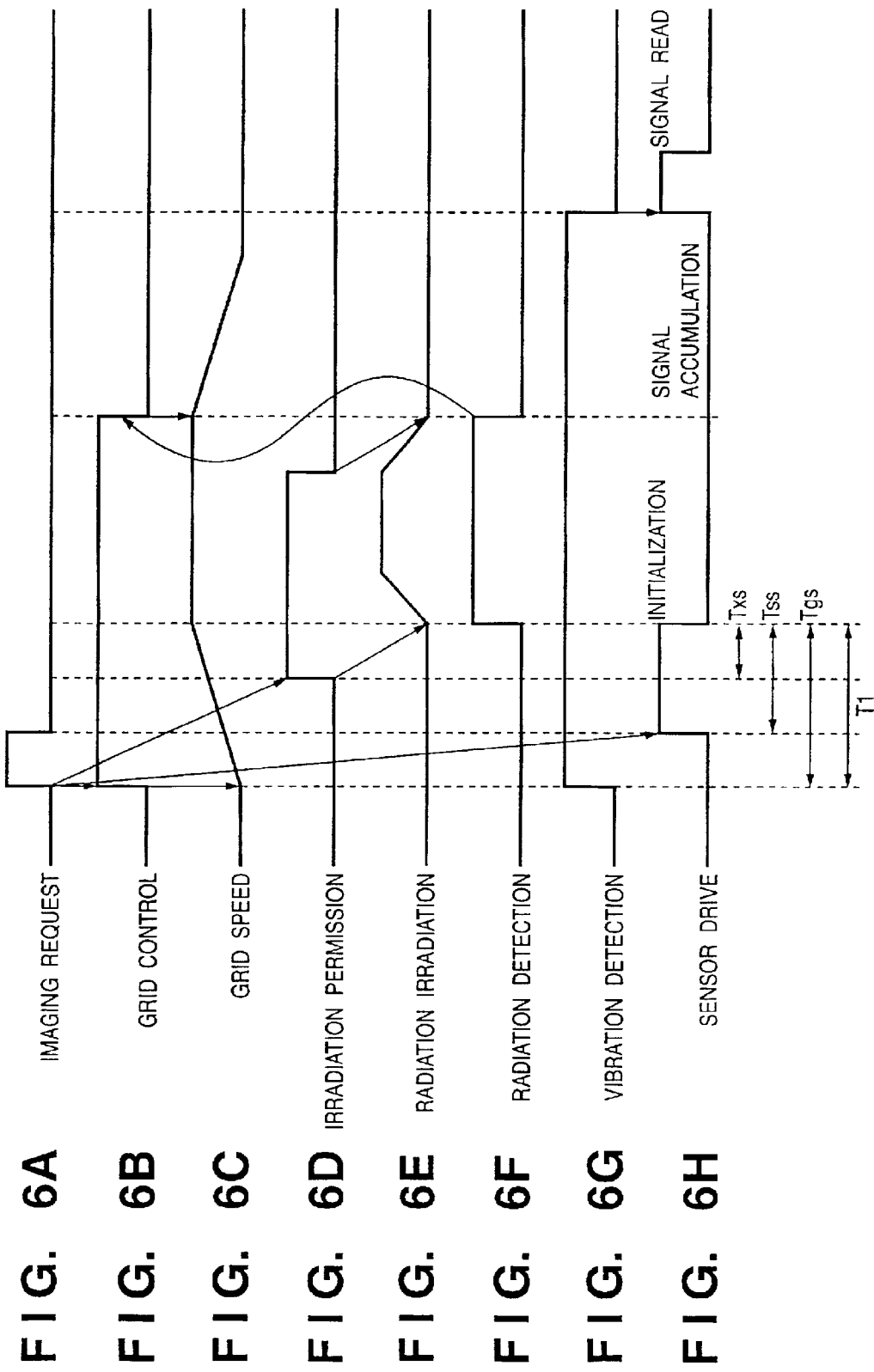

IMAGING APPARATUS, IMAGING SYSTEM, CONTROL METHOD OF IMAGING APPARATUS, AND STORAGE MEDIUM WITH TIMING CONTROL FUNCTIONALITY

FIELD OF THE INVENTION

The present invention relates to an imaging apparatus, imaging system, imaging control method, and computer-readable storage medium which stores processing steps in executing the method, which are used for, e.g., an apparatus or system for performing radiation imaging of an object using a grid.

BACKGROUND OF THE INVENTION

Conventionally, a radiation method may involve irradiating an object with radiation such as X-rays and detecting the intensity distribution of the radiation transmitted through the object to acquire the radiation image of the object. This method is widely used in the field of industrial non-destructive inspection or medical diagnosis.

In the most popular radiation imaging method, a combination of a so-called "phosphor plate" (or "sensitized paper") which emits fluorescent light by radiation and a silver halide film is used.

In the above radiation imaging method, first, an object is irradiated with radiation. The radiation transmitted through the object is converted into visible light by the phosphor plate to form a latent image on the silver halide film. After that, the silver halide film is chemically processed to acquire a visible image.

A thus obtained film image (radiation image) is a so-called analog picture and is used for medical diagnosis or inspection.

A computed radiography apparatus (referred to as a "CR apparatus" hereinafter) which acquires a radiation image using an imaging plate (referred to as an "IP" hereinafter) coated with a stimulable phosphor as a phosphor is also being put into practice.

When an IP primarily excited by radiation irradiation is secondarily excited by visible light such as a red laser beam, light called stimulable fluorescent light is emitted. The CR apparatus detects this light emission using a photosensor such as a photomultiplier to acquire a radiation image and outputs a visible image to a photosensitive material or CRT on the basis of the radiation image data.

Although the CR apparatus is a digital imaging apparatus, it is regarded as an indirect digital imaging apparatus because the image formation process, reading by secondary excitation, is necessary. The reason for "indirect" is that the apparatus cannot instantaneously display the radiation image, like the above-described apparatus (referred to as an "analog imaging apparatus" hereinafter) which acquires an analog radiation image such as an analog picture.

In recent years, a technique has been developed, which acquires a digital radiation image using a photoelectric conversion device in which pixels formed from small photoelectric conversion elements or switching elements are arrayed in a matrix as an image detection means for acquiring a radiation image from radiation through an object.

Examples of a radiation imaging apparatus employing the above technique, i.e., having phosphors stacked on a sensor such as a CCD or amorphous silicon two-dimensional image sensing element are disclosed in U.S. Pat. Nos. 5,418,377, 5,396,072, 5,381,014, 5,132,539, and 4,810,881.

Such a radiation imaging apparatus can instantaneously display acquired radiation image data and is therefore regarded as a direct digital imaging apparatus.

As advantages of the indirect or direct digital imaging apparatus over the analog imaging apparatus, it becomes possible to provide a filmless system, an increase in acquired information by image processing, and database construction.

An advantage of the direct digital imaging apparatus over the indirect digital imaging apparatus is instantaneity. The direct digital imaging apparatus can be effectively used on, e.g., a medical scene with urgent need because a radiation image obtained by imaging can be immediately displayed at that place.

When the radiation imaging apparatus described above is used as a medical apparatus to detect the radiation transmission density of a patient as an object to be examined, a scattering ray removing member called a "grid" is normally inserted between the patient and a radiation transmission density detector (also simply referred to as a "detector" hereinafter) to reduce the influence of scattering rays generated when radiation is transmitted through the person to be examined.

A grid is formed by alternately arranging a thin foil of a material such as lead which hardly passes radiation and that of a material such as aluminum which readily passes radiation perpendicularly to the irradiation direction of radiation.

With this structure, radiation components such as scattering rays in the patient, which are generated when the patient is irradiated with radiation and have angles with respect to the axis of irradiation, are absorbed by the lead foil in the grid before they reach the detector. For this reason, a high-contrast image can be obtained.

If the grid stands still during imaging, the radiation reaching the lead in the grid is wholly absorbed including both the scattering rays and the primary rays of radiation. Since a density difference distribution corresponding to the array in the grid is formed at the detection section, a striped radiation image is detected, resulting in inconvenience in reading at the time of image diagnosis or the like.

A radiation imaging apparatus having a mechanism for moving the grid during imaging has already been placed on the market.

However, since the above-described conventional digital radiation imaging apparatus is designed to execute discrete sampling, interference called "moire" may take place for a periodical image such as stripes of the grid (this phenomenon will be referred to as "grid stripe image formation on the object" hereinafter).

Especially when a reduced radiation image is displayed, the period of moire changes in various ways depending on the reduction magnification and adversely affects reading at the time of image diagnosis or the like.

To avoid the problem of grid stripe image formation on the object as described above, the grid stripe image formation on the object must be sufficiently reduced by more strictly managing grid movement than in the analog imaging apparatus.

More specifically, a radiation generator generally has a delay time of several ten to several hundred ms from a radiation irradiation instruction (instruction by pressing the imaging button and also referred to as an "imaging request" hereinafter) from the user to actual radiation irradiation (also referred to as "actual irradiation" hereinafter). This delay time changes between radiation tubes and between devices (radiation generators) for generating radiation by the radiation tubes.

Hence, to avoid the problem of grid stripe image formation on the object, the position and speed of the grid must be controlled in consideration of the delay time corresponding to the radiation tube and radiation generator used for radiation imaging. Neither an apparatus nor system that implements such control are conventionally available.

Additionally, in radiation imaging aiming at, e.g., image diagnosis, since the positional relationship between internal organs represented by lungs and diaphragm largely contributes to the image diagnostic performance, the imaging timing is very important.

For this reason, the user must issue an imaging request while observing the movement of the object and control the radiation imaging apparatus as soon as possible for the imaging request. However, after the imaging request, the sensor such as a two-dimensional solid-state image sensing element and the grid must be initialized. Each initialization takes several ten to several hundred ms.

Although the time delay from the imaging request to actual irradiation is preferably shortened by parallelly performing control of the radiation imaging apparatus and initialization of the sensor and grid, neither an apparatus nor system that implements such control are conventionally available.

SUMMARY OF THE INVENTION

The present invention has been made to solve the above problems, and has as its object to provide an imaging apparatus, imaging system, imaging control method, and computer-readable storage medium which stores processing steps of executing the method, which can provide a satisfactory image at a desired imaging timing by implementing grid movement control according to the time response characteristics of the radiation generation function and a decrease in time delay from an imaging request to actual irradiation.

In order to achieve the above object, an imaging apparatus according to the first aspect of the present invention is characterized by the following arrangement.

That is, there is provided an imaging apparatus having a function of irradiating an object with irradiation means and sensing light transmitted through the object with image sensing means, comprising control means for controlling an actual irradiation instruction timing for the irradiation means on the basis of a pre-irradiation delay time as a time between an instruction and irradiation of actual irradiation of the irradiation means.

An imaging system according to the first aspect of the present invention is characterized by the following arrangement.

That is, there is provided an imaging system in which a plurality of devices are communicably connected, wherein at least one of the plurality of devices has the function of the imaging apparatus which controls an actual irradiation instruction timing for irradiation means on the basis of a pre-irradiation delay time as a time between an instruction and irradiation of actual irradiation of the irradiation means.

An imaging apparatus according to the second aspect of the present invention is characterized by the following arrangement.

That is, there is provided an imaging apparatus having a function of irradiating an object with irradiation means and sensing light transmitted through the object with image sensing means through a movable grid, comprising control means for controlling an actual irradiation instruction timing for the irradiation means on the basis of an initialization time of grid movement.

An imaging system according to the second aspect of the present invention is characterized by the following arrangement.

That is, there is provided an imaging system in which a plurality of devices are communicably connected, wherein at least one of the plurality of devices has the function of the imaging apparatus which controls an actual irradiation instruction timing for irradiation means on the basis of an initialization time of grid movement.

An imaging control method according to the first aspect of the present invention is characterized by the following step.

That is, there is provided an imaging control method of irradiating an object with irradiation means and sensing light transmitted through the object with image sensing means, comprising the step of controlling an actual irradiation instruction timing for the irradiation means on the basis of a pre-irradiation delay time as a time between an instruction and irradiation of actual irradiation of the irradiation means.

An imaging control method according to the second aspect of the present invention is characterized by the following step.

That is, there is provided an imaging control method of irradiating an object with irradiation means and sensing light transmitted through the object with image sensing means through a movable grid, comprising the step of controlling an actual irradiation instruction timing for the irradiation means on the basis of an initialization time of grid movement.

A storage medium of the present invention is a computer-readable storage medium characterized in that the storage medium stores a processing program for executing the imaging control method.

Other objects and advantages besides those discussed above shall be apparent to those skilled in the art for the description of a preferred embodiment of the invention which follows. In the description, reference is made to accompanying drawings, which form a part hereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

FIG. 5 is a flow chart for explaining operation of the radiation imaging system; and FIGS. 6A to 6H are timing charts for explaining the operation control timing of the radiation imaging system.

DETAILED DESCRIPTION OF THE PREFERRED EMBODIMENTS

The embodiments of the present invention will be described below with reference to the accompanying drawings.

(First Embodiment)

Figure 1:
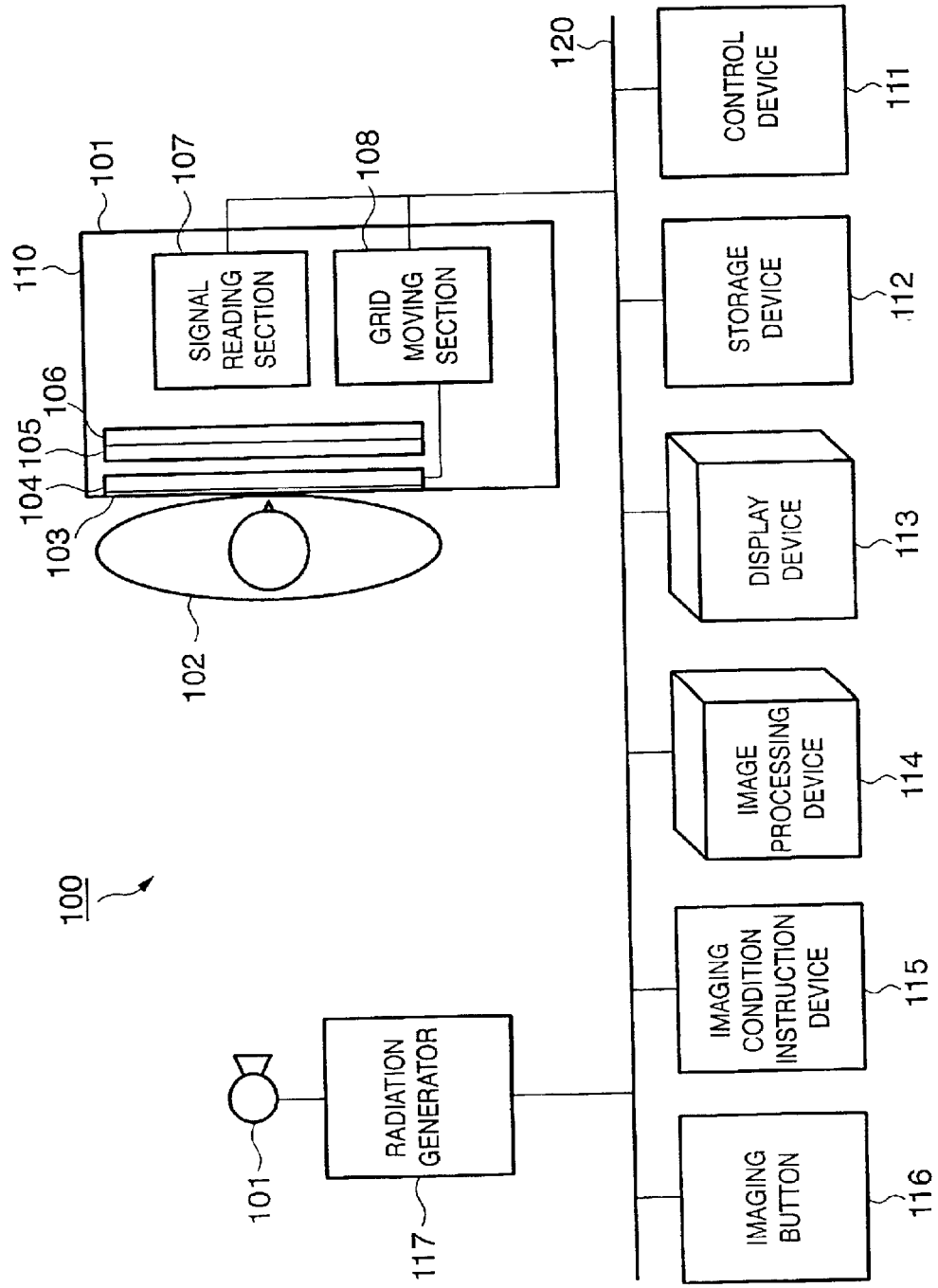
FIG. 1 is a block diagram showing the arrangement of a radiation imaging system according to the first embodiment, to which the present invention is applied.

The present invention is applied to, e.g., a radiation imaging system 100 as shown in FIG. 1.

<Arrangement of Radiation Imaging System 100>

As shown in FIG. 1, the radiation imaging system 100 has an arrangement including an imaging device 110 for acquiring an image signal of an object (patient) 102 to be examined, a control device 111 for controlling the entire system 100, a storage device 112 for storing various data such as a control program for control processing by the control device 111 and the image, a display device 113 for displaying the image or the like, an image processing device 114 for executing arbitrary image processing for the image signal of the patient 102, which is obtained by the imaging device 110, an imaging condition instruction device 115 for instructing various imaging conditions in the imaging device 110, an imaging button 116 for instructing the system 100 to start imaging operation, and a radiation generator 117 for generating a radiation (e.g., X-rays) from a radiation tube 101 to the patient 102. The devices or components are connected to each other through a system bus 120 to exchange data.

The imaging device 110 is located at a position where the radiation generated from the radiation tube 101 of the radiation generator 117 can be received through the patient 102. The imaging device 110 comprises a chest stand 103, grid 104, phosphor 105, sensor (two-dimensional solid-state image sensing element) 106, signal reading section 107, and grid moving section 108.

The chest stand 103, grid 104, phosphor 105, and sensor 106 are arranged in this order from the side of the radiation tube 101 of the radiation generator 117.

<Series of Operations of Radiation Imaging System 100>

Outlines of the imaging procedure and radiation image generation process in the radiation imaging system 100 will be described here.

The user (e.g., radiation technician) positions the patient 102 to the chest stand 103 and selectively inputs appropriate imaging conditions (e.g., tube voltage, tube current, irradiation time, type of sensor 106, and type of radiation tube 101) using the imaging condition instruction device 115.

In this embodiment, the imaging conditions are manually inputted by the user through the imaging condition instruction device 115. However, the present invention is not limited to this.

For example, the imaging conditions may be inputted through a network (not shown) connected to the imaging device 110.

Next, the user presses the imaging button 116 to request the control device 111 to start imaging operation.

After receiving the imaging operation start request from the user, the control device 111 performs initialization necessary in the system 100 and prompts the radiation generator 117 to irradiate the person with radiation.

In accordance with the irradiation instruction from the control device 111, the radiation generator 117 generates radiation from the radiation tube 101.

The radiation generated from the radiation tube 101 passes through the patient 102 and reaches chest stand 103.

The chest stand 103 is exposed by the radiation transmitted through the patient 102 with a transmitted radiation distribution in accordance with the structure in the patient 102.

Since the chest stand 103 is sufficiently transparent to the radiation, the radiation transmitted through the chest stand 103 reaches the grid 104.

The grid 104 removes scattering ray components in the radiation transmitted through the chest stand 103 and sends only effective radiation components to the phosphor 185.

The phosphor 105 converts the radiation (effective radiation) from the grid 104 into visible light in accordance with the spectral sensitivity of the sensor 106.

The sensor 106 receives the radiation from the phosphor 105, converts the radiation light into an electrical signal (image signal) by two-dimensional photoelectric conversion, and accumulates it.

The signal reading section 107 reads out the image signal accumulated in the sensor 106 and stores the signal in the storage device 112 as a radiation image signal.

The image processing device 114 performs appropriate image processing for the radiation image signal stored in the storage device 112.

The display device 113 displays the radiation image signal after processing by the image processing device 114.

<Most Characteristic Operation and Arrangement of Radiation Imaging System 100>

Figure 2:
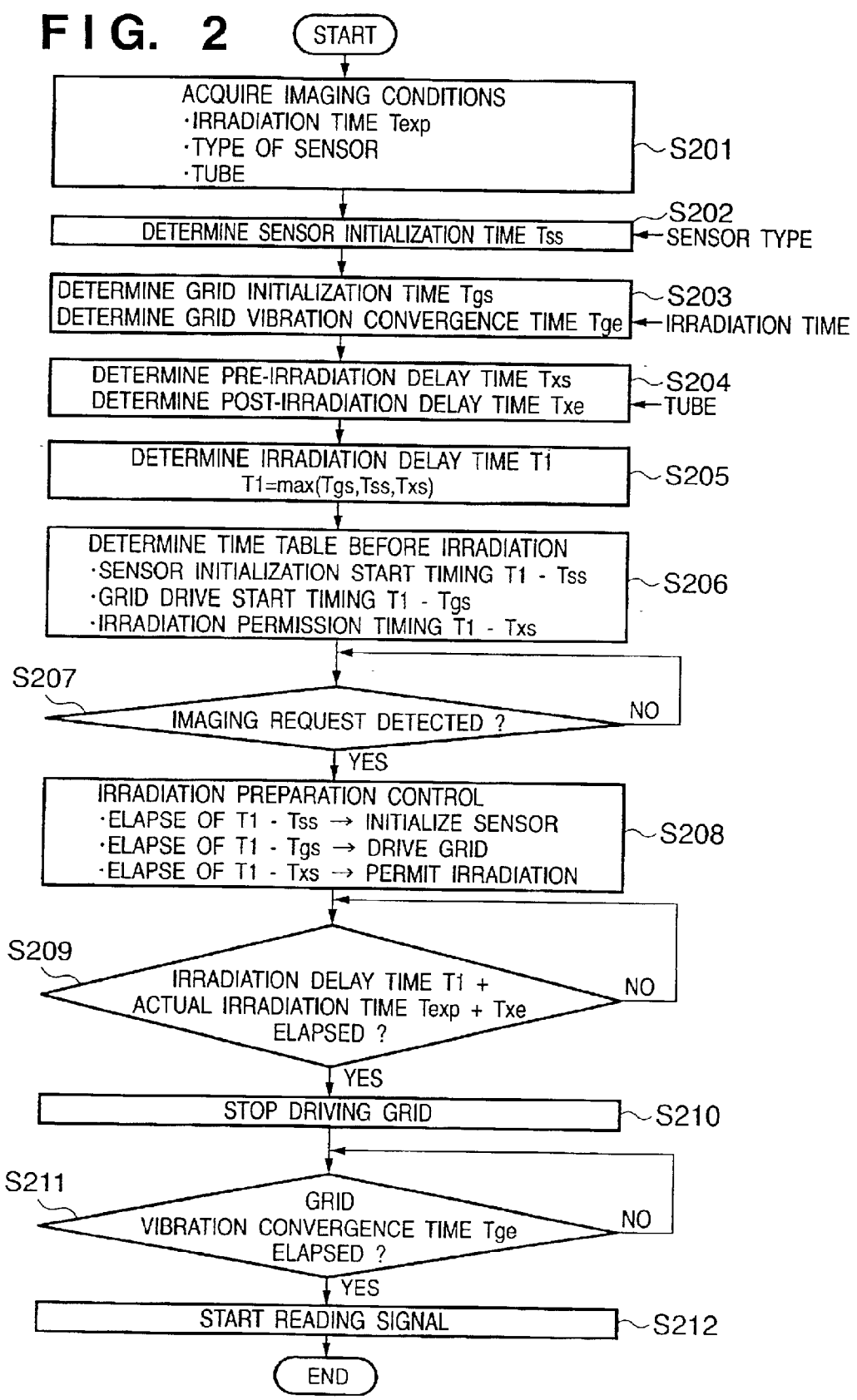
FIG. 2 is a flow chart for explaining operation of the radiation imaging system.

FIG. 2 is a flow chart showing operation control processing executed by the control device 111 for the system 100. FIGS. 3A to 3F are timing charts showing the operation control timing.

The processing shown in FIG. 2 corresponds to processing from the above-described imaging condition input by the user to image signal read from the sensor 106.

Step S201:

The control device 111 recognizes an irradiation time Texp, the type of sensor 106 used for imaging, and the type of radiation tube 101 on the basis of imaging conditions selectively input by the user through the imaging condition instruction device 115.

In accordance with the recognized information, the control device 111 determines control until radiation irradiation and control after radiation irradiation by processing from step S202.

Step S202:

The control device 111 determines a sensor initialization time Tss in accordance with the type of sensor 106.

The sensor initialization time Tss changes depending on the type of sensor 106. For example, when the sensor 106 requires predischarge of a dark current, the pre-read time is the sensor initialization time Tss. From this time, signal accumulation in the sensor 106 starts.

Step S203:

The control device 111 determines a grid initialization time Tgs and grid oscillation convergence time Tge from the irradiation time Texp.

More specifically, to reduce stripe image formation on the object by the grid 104, for example, radiation must be transmitted through stripes of 10 or more cycles. However, the moving distance of the grid 104 is limited. Hence, the moving speed of the grid 104 must be optimized in accordance with the irradiation time Texp. In addition, since the grid 104 generally has a focal point, the irradiation central position of radiation and the central position of the grid 104 must be aligned to obtain an image with a satisfactory quality.

Hence, a time required until the optimum moving speed (target moving speed) of the grid 104 is obtained, and the position of the grid 104 reaches the irradiation central position (target position) of radiation corresponds to the grid initialization time Tgs.

In this embodiment, the grid initialization times Tgs until the target moving speed and position of the grid 104 are obtained and the grid oscillation convergence times Tge required to converge device oscillation caused by movement are obtained as a table by experiments in correspondence with, e.g., various patterns of irradiation time Texp and moving speed of the grid 104 and stored in the storage device 112 in advance. The grid initialization time Tgs and grid oscillation convergence time Tge corresponding to the actually obtained irradiation time Texp are determined from the table information in the storage device 112.

Step S204:

The control device 111 determines a pre-irradiation delay time Txs and post-irradiation delay time Txe on the basis of the type of radiation tube 101.

The pre-irradiation delay time Txs is a time after the radiation generator 117 is instructed to permit radiation irradiation until the radiation generator 117 actually starts radiation irradiation, and is determined by the type of radiation generator 117 or radiation tube 101.

In this embodiment, the pre-irradiation delay times Txs corresponding to, e.g., various types of radiation generator 117 or radiation tube 101 are prepared as a table in advance, and a corresponding pre-irradiation delay time Txs is determined from the table information.

The post-irradiation delay time Txe is a delay time after the elapse of irradiation time Texp until the radiation generator 117 actually ends the radiation irradiation. The post-irradiation delay time Txe is also determined in accordance with the same procedure as that for the pre-irradiation delay time Txs.

Step S205:

The control device 111 determines an irradiation delay time T1.

The irradiation delay time T1 is a delay time after an imaging request is input by the user through the imaging button 116 until the radiation generator 117 actually starts radiation irradiation. Of the sensor initialization time Tss determined in step S202, the grid initialization time Tgs determined in step S203, and the pre-irradiation delay time Txs determined in step S204, the longest time is determined as the irradiation delay time T1.

Step S206:

The control device 111 determines a time table before irradiation.

This time table is determined from the sensor initialization time Tss determined in step S202, the grid initialization time Tgs determined in step S203, and the pre-irradiation delay time Txs determined in step S204.

More specifically, the control sequence and times (timings) of initialization of the sensor 106, start of drive of the grid 104, and radiation irradiation instruction (irradiation permission) to the radiation generator 117 after the imaging request input by the user through the imaging button 116 is recognized are determined by subtracting each delay time from the irradiation delay time T1 determined in step S205.

The initialization timing of the sensor 106 is determined as "T1−Tss". The drive start timing of the grid 104 is determined as "T1−Tgs". The radiation irradiation instruction (irradiation permission) timing for the radiation generator 117 is determined as "T1−Txs".

Step S207:

After control before radiation irradiation is determined in the above-described way, the control device 111 determines whether an imaging request is input by the user through the imaging button 116 and stands by until an imaging request is received.

Step S208:

Upon recognizing that an imaging request is input by the user through the imaging button 116, the control device 111 executes operation control according to the time table determined in step S206.

Initialization of the sensor 106 is started after the elapse of "T1−Tss", drive of the grid 104 is started after the elapse of "T1−Tgs", and irradiation permission is executed after the elapse of "T1−Txs".

Step S209:

The control device 111 stands by until the total time (T1+Texp+Txe) of the irradiation time (actual exposure time) Texp determined in step S201, the post-irradiation delay time Txe determined in step S204, and the irradiation delay time T1 determined in step S205 elapses.

Step S210:

When recognizing that the time (T1+Texp+Txe) has elapsed, the control device 111 stops driving the grid 104 through the grid moving section 108.

Step S211:

The control device 111 stands by until the grid oscillation convergence time Tge determined in step S203 elapses.

Step S212:

When recognizing that the grid oscillation convergence time Tge has elapsed, the control device 111 causes the signal reading section 107 to start reading out the signal accumulated in the sensor 106.

In the operation control for the radiation imaging system 100 shown in the flow chart of FIG. 2, especially, since the operation stands by for the post-irradiation delay time Txe after the elapse of irradiation time Texp, stripe image formation on the object by the grid 104 can be prevented.

In addition, since drive of the grid 104 is stopped, the influence of electromagnetic noise generated from the grid moving section 108 can be prevented.

Furthermore, since the operation stands by for the grid oscillation convergence time Tge after the stop of drive of the grid 104, the influence of device oscillation can be prevented.

Hence, after the imaging request from the user is recognized, the control device 111 controls the operation of the system 100 in accordance with the flow chart in FIG. 2, thereby acquiring a satisfactory image.

The above operation control for the radiation imaging system 100 will be described below in more detail with reference to the timing charts shown in FIGS. 3A to 3F.

The timing charts of FIGS. 3A to 3F explain timings after the imaging button 116 is pressed.

In accordance with the imaging conditions input by the user, for example,

Irradiation time Texp=100 ms

Sensor initialization time Tss=200 ms

Grid initialization time Tgs=300 ms

Pre-irradiation delay time Txs=100 ms

Grid oscillation convergence time Tge=300 ms

Post-irradiation delay time Txe=100 ms are determined.

In this case, the irradiation delay time T1 is the longest time of the sensor initialization time Tss, grid initialization time Tgs, and pre-irradiation delay time Txs and is determined by $T1 = \max(Tss, Tgs, Txs) = Tgs = 300$ ms.

Operation control until radiation irradiation is determined from these initial conditions.

Next, control timings for sensor initialization, start of grid movement, and irradiation permission instruction after recognition of the imaging request are determined by subtracting a corresponding time required for operation from the irradiation delay time T1.

Sensor initialization timing: T1−Tss 100 ms

Grid movement start timing: T1−Tgs 0 ms

Irradiation enable signal transmission timing:

T1−Txs=200 ms

Control timings after radiation irradiation are so determined that movement control for the grid 104 is stopped after the elapse of actual irradiation time obtained by adding the irradiation time Texp and post-irradiation delay time Txe to the irradiation delay T1, and the signal read from the sensor 106 is started after the elapse of grid oscillation convergence time Tge.

That is, the grid control stop timing and signal read start timing are determined by Grid control stop timing: T1+Texp+Txe=500 ms Signal read start timing: T1+Texp+Txe+Tge=800 ms After the control timings are determined, an imaging request (FIG. 3A) input by the user by pressing the imaging button 116 is waited upon.

When an imaging request is recognized, operation control for the radiation imaging system 100 is started on the basis of the determined control timings.

Figure 3:
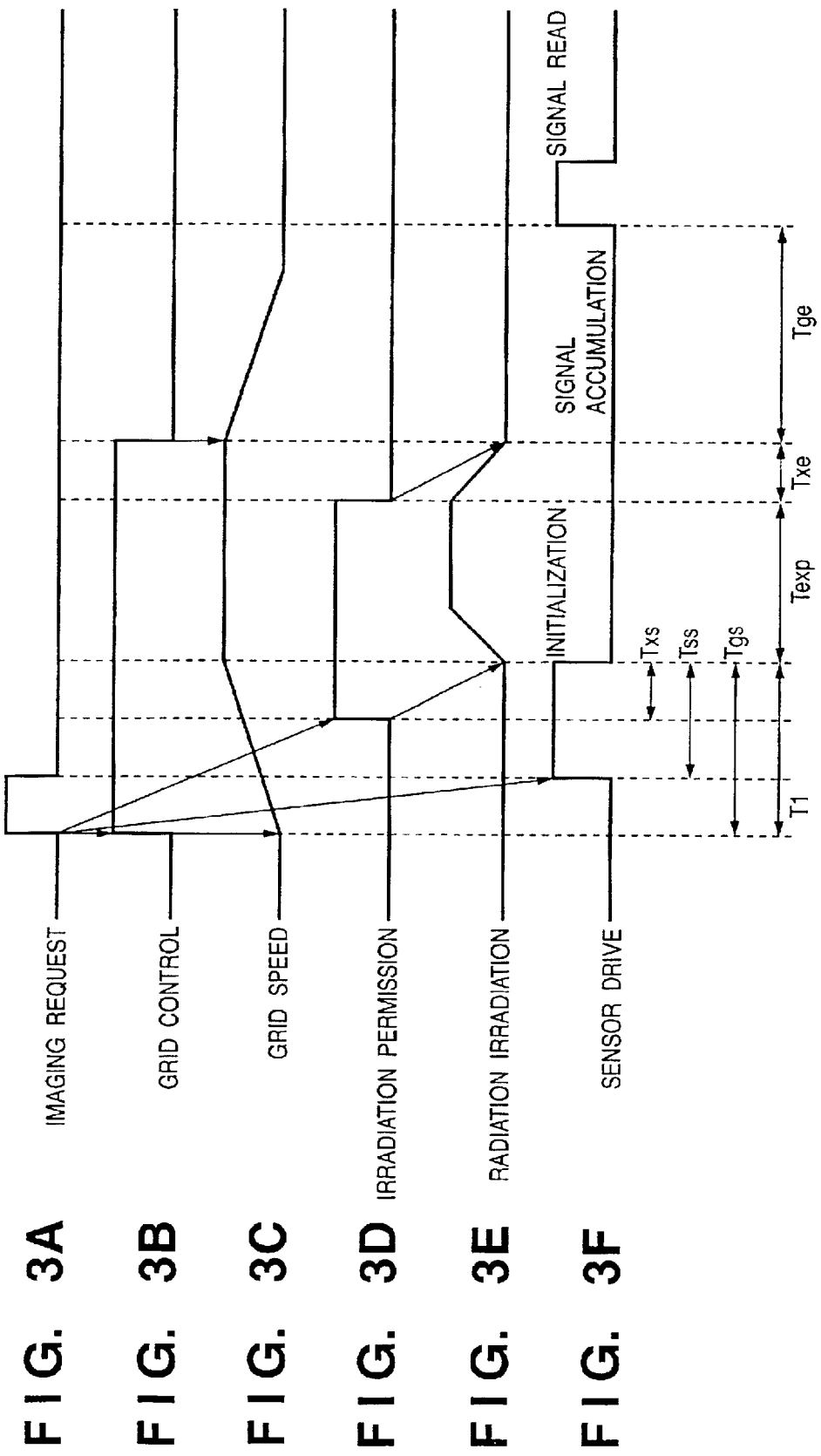
FIGS. 3A to 3F are timing charts for explaining the operation control timing of the radiation imaging system.

First, movement (motion) of the grid 104 is started, as shown in FIG. 3B.

The moving speed of the grid 104 acceleratingly increases and reaches an irradiation enable state after the elapse of 300 ms (grid initialization time Tgs=300 ms), as shown in FIG. 3C.

Next, as shown in FIG. 3F, after the elapse of 100 ms (sensor initialization timing: T1−Tss=100 ms) from imaging request recognition, initialization of the sensor 106 is started. After the elapse of 200 ms (sensor initialization time Tss=200 ms), initialization of the sensor 106 is ended.

As shown in FIG. 3D, after the elapse of 200 ms (irradiation enable signal transmission timing: T1−Txs=200 ms) from imaging request recognition, the radiation generator 117 is instructed to start irradiation.

The radiation generator 117 starts actual irradiation after the elapse of 100 ms (preirradiation delay time Txs=100 ms), as shown in FIG. 3E. The end timing of sensor initialization (end timing of the sensor initialization time Tss), the end timing of grid movement (end timing of the grid initialization time Tgs), and the end timing of irradiation enable signal transmission (end timing of the pre-irradiation delay time Txs) match the end timing of the irradiation delay time T1 from the imaging request to actual irradiation.

After the elapse of 500 ms (grid control stop timing: T1+Texp+Txe=500 ms) from imaging request recognition, actual irradiation by the radiation generator 117 is ended.

At this time, movement control for the grid 104 is stopped, as shown in FIG. 3B, and the moving speed of the grid 104 gradually decreases. Along with this deceleration, the oscillation of the imaging device 110, that is generated by moving the grid 104, starts converging.

After that, as shown in FIG. 3F, after the elapse of 800 ms (signal read start timing: T1+Texp+Txe+Tge=800 ms) from imaging request recognition, the signal reading section 107 is instructed to end signal accumulation in the sensor 106 and start reading the signal.

At this time, the oscillation of the imaging device 110 has become so small that it does not affect the image quality. As a result, a satisfactory image can be obtained.

(Second Embodiment)

Figure 4:
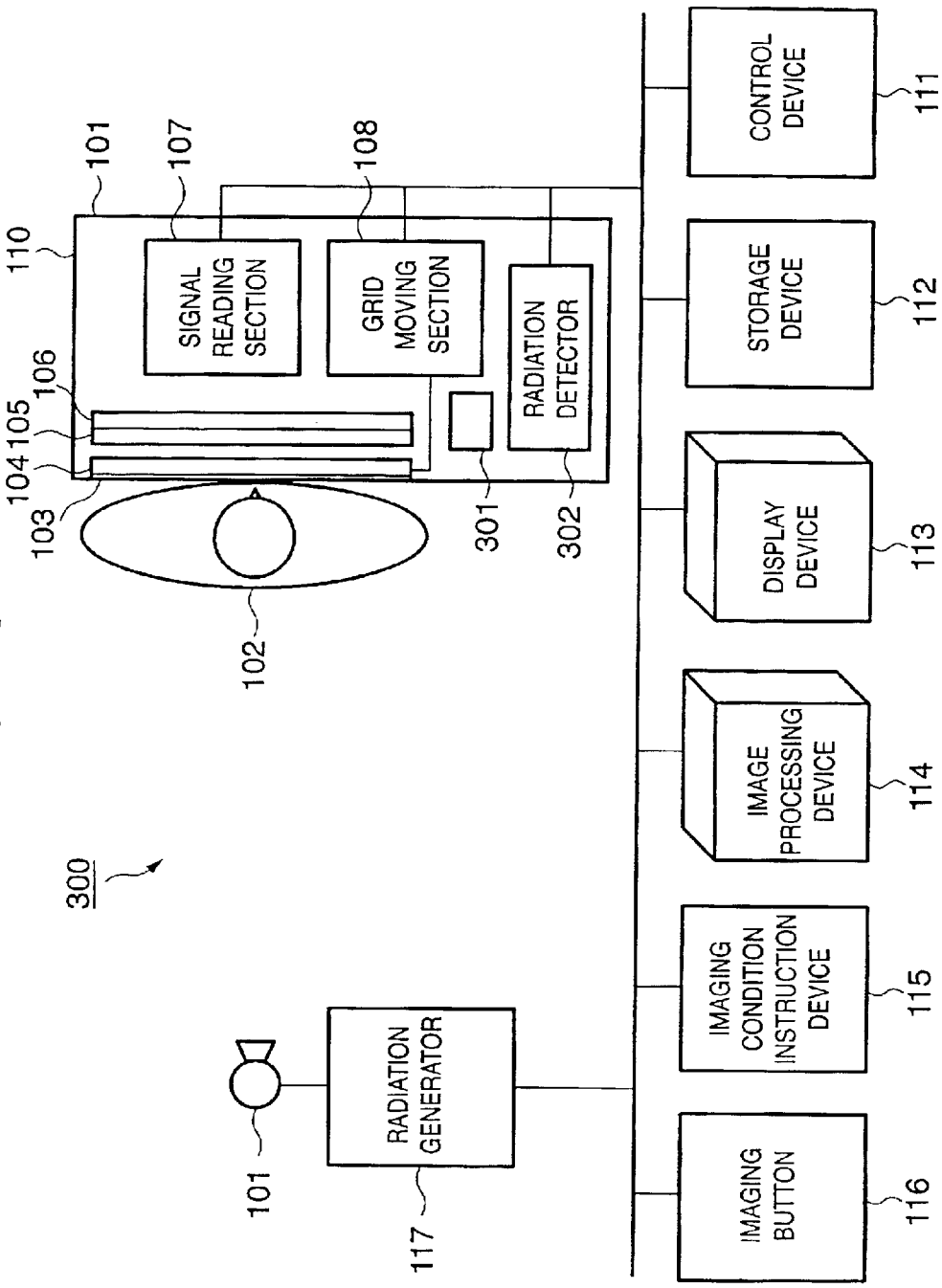
FIG. 4 is a block diagram showing the arrangement of a radiation imaging system according to the second embodiment, to which the present invention is applied.

The present invention is applied to, e.g., a radiation imaging system 300 as shown in FIG. 4.

This radiation imaging system 300 has the same arrangement as that of the radiation imaging system 100 shown in FIG. 1 except that a radiation detector 302 for detecting a radiation irradiation state and an oscillation measurement device 301 for measuring the oscillation state of a grid 104 are prepared in an imaging device 110.

The same reference numerals as in the radiation imaging system 100 shown in FIG. 1 denote the same parts in the radiation imaging system 300 shown in FIG. 4, and a detailed description thereof will be omitted. Only parts different from the radiation imaging system 100 in FIG. 1 will be described in detail.

FIG. 5 is a flow chart showing operation control processing executed by a control device 111 of this embodiment for the system 300. FIGS. 6A to 6H are timing charts showing the operation control timing.

The same step numbers as in the flow chart of FIG. 2 denote the same processing steps in the flow chart of FIG. 5, and a detailed description thereof will be omitted.

Step S201:

The control device 111 recognizes an irradiation time Texp, the type of sensor 106 used for imaging, and the type of radiation tube 101 on the basis of imaging conditions selectively input by the user through an imaging condition instruction device 115.

In accordance with the recognized information, the control device 111 determines control until radiation irradiation and control after radiation irradiation by processing from step S202.

Step S202:

The control device 111 determines a sensor initialization time Tss in accordance with the type of sensor 106.

Step S203':

The control device 111 determines a grid initialization time Tgs (time until the grid 104 reaches the target moving speed and position) from the irradiation time Texp.

Step S204':

The control device 111 determines a pre-irradiation delay time Txs (time after radiation irradiation permission is instructed to a radiation generator 117 until the radiation generator 117 actually starts radiation irradiation) on the basis of the type of radiation tube 101.

Step S205:

The control device 111 determines an irradiation delay time T1 (the longest time of the sensor initialization time Tss, grid initialization time Tgs, and pre-irradiation delay time Txs).

Step S206:

The control device 111 determines, as a time table before irradiation, the initialization timing of the sensor 106 as "T1−Tss", the drive start timing of the grid 104 as "T1−Tgs", and the radiation irradiation instruction (irradiation permission) timing for the radiation generator 117 as "T1−Txs".

Step S207:

After control before radiation irradiation is determined in the above-described way, the control device 111 determines whether an imaging request is input by the user through an imaging button 116 and stands by until an imaging request is received.

Step S208:

Upon recognizing that an imaging request is input by the user through the imaging button 116, the control device 111 executes operation control according to the time table determined in step S206.

Initialization of the sensor 106 is started after the elapse of "T1−Tss". Drive of the grid 104 is started after the elapse of "T1−Tgs". Irradiation permission is executed after the elapse of "T1−Txs".

Step S209':

The control device 111 determines on the basis of a detection signal output from the radiation detector 302 whether radiation irradiation by the radiation generator 117 is ended.

Step S210:

Upon recognizing that radiation irradiation by the radiation generator 117 is ended, the control device 111 stops driving the grid 104 through a grid moving section 108.

Step S211':

The control device 111 determines on the basis of a measurement result from the oscillation measurement device 301 whether the oscillation of the grid 104 has converged.

Step S212:

When recognizing that the oscillation of the grid 104 has converged, the control device 111 causes a signal reading section 107 to start reading out the signal accumulated in the sensor 106.

In the operation control for the radiation imaging system 300 shown in the flow chart of FIG. 5, especially when the end of radiation irradiation is recognized in accordance with the detection result from the radiation detector 302, drive of the grid 104 is stopped. For this reason, the influence of electromagnetic noise generated from the grid moving section 108 can be prevented.

Furthermore, since the operation stands until it is determined on the basis of the measurement result from the oscillation measurement device 301 that the oscillation of the grid 104 has converged after the stop of drive of the grid 104, the influence of device oscillation can be prevented.

Hence, after the imaging request from the user is recognized, the control device 111 controls the operation of the system 300 in accordance with the flow chart in FIG. 5, thereby acquiring a satisfactory image.

The above operation control for the radiation imaging system 300 will be described below in more detail with reference to the timing charts shown in FIGS. 6A to 6H.

The timing charts of FIGS. 6A to 6H explain timings after the imaging button 116 is pressed.

In accordance with the imaging conditions input by the user, for example,

Irradiation time Texp=100 ms

Sensor initialization time Tss=200 ms

Grid initialization time Tgs=300 ms

Pre-irradiation delay time Txs=100 ms are determined.

In this case, the irradiation delay time T1 is the longest time of the sensor initialization time Tss, grid initialization time Tgs, and pre-irradiation delay time Txs and is determined by $$T1=\max(Tss, Tgs, Txs)=Tgs=300 \text{ ms}.$$

Operation control until radiation irradiation is determined from these initial conditions.

Next, control timings for sensor initialization, start of grid movement, and irradiation permission instruction after recognition of the imaging request are determined by subtracting a corresponding time required for operation from the irradiation delay time T1.

Sensor initialization timing: T1 Tss=100 ms

Grid movement start timing: T1 Tgs=0 ms

Irradiation enable signal transmission timing: T1−Txs= 200 ms

After the control timings are determined, an imaging request (FIG. 6A) input by the user by pressing the imaging button 116 is waited upon.

When an imaging request is recognized, operation control for the radiation imaging system 300 is started on the basis of the determined control timings.

First, movement (motion) of the grid 104 is started, as shown in FIG. 6B. Simultaneously, the oscillation detection signal representing that the grid 104 is in a moving state is set at High level, as shown in FIG. 6G.

The moving speed of the grid 104 acceleratingly increases and reaches an irradiation enable state after the elapse of 300 ms (grid initialization time Tgs=300 ms), as shown in FIG. 6C.

Next, as shown in FIG. 6H, after the elapse of 100 ms (sensor initialization timing: T1−Tss=100 ms) from imaging request recognition, initialization of the sensor 106 is started. After the elapse of 200 ms (sensor initialization time Tss=200 ms), initialization of the sensor 106 is ended.

As shown in FIG. 6D, after the elapse of 200 ms (irradiation enable signal transmission timing: T1−Txs=200 ms) from imaging request recognition, the radiation generator 117 is instructed to start irradiation.

The radiation generator 117 starts actual irradiation after the elapse of 100 ms (pre-irradiation delay time Txs=100 ms), as shown in FIG. 6E. Simultaneously, the radiation detection signal representing radiation irradiation is set at High level, as shown in FIG. 6F.

When radiation irradiation is ended, and the output from the radiation detector 302 becomes smaller than a predetermined threshold value, it is determined that irradiation is ended. As shown in FIG. 6F, the radiation detection signal is set at Low level. Along with this processing, movement control for the grid 104 is stopped, as shown in FIG. 6B. The moving speed of the grid 104 gradually decreases. The oscillation state of the grid 104 at this time is observed by the oscillation measurement device 301.

When the oscillation of the imaging device 110, that is generated by moving the grid 104, starts converging, and it is recognized that the output from the oscillation measurement device 301 becomes smaller than a predetermined oscillation amount, the oscillation detection signal is set at Low level, as shown in FIG. 6G.

As shown in FIG. 6F, the signal reading section 107 is instructed to end signal accumulation in the sensor 106 and start reading the signal.

At this time, the oscillation of the imaging device 110 has become so small that it does not affect the image quality. As a result, a satisfactory image can be obtained.

The object of the present invention is achieved even by supplying a storage medium which stores software program codes for implementing the functions of the first and second embodiments in a system or apparatus and causing the computer (or a CPU or MPU) of the system or apparatus to read out and execute the program codes stored in the storage medium.

In this case, the program codes read out from the storage medium implement the functions of the first and second embodiments by themselves, and the storage medium which stores the program codes constitutes the present invention.

As a storage medium for supplying the program codes, for example, a ROM, a floppy disk, hard disk, optical disk, magnetooptical disk, CD-ROM, CD-R, magnetic tape, nonvolatile memory card or the like can be used.

The functions of the first and second embodiments are implemented not only when the readout program codes are executed by the computer, but also when the operating system (OS) running on the computer performs part or all of actual processing on the basis of the instructions of the program codes.

The functions of the first and second embodiments are also implemented when the program codes read out from the storage medium are written in the memory of a function expansion board inserted into the computer or a function expansion unit connected to the computer. The CPU of the function expansion board or function expansion unit performs part or all of actual processing on the basis of the instructions of the program codes.

As has been described above, in the above embodiments, the timing when the irradiation means is permitted to perform irradiation is determined from the initialization time of the image sensing means (e.g., two-dimensional solid-state image sensing element) and the irradiation delay time (delay time after irradiation execution instruction, i.e., irradiation permission is issued until actual irradiation is performed) of the irradiation means (e.g., radiation generation means). Therefore, imaging operation control for an imaging request and initialization of the image sensing element can be parallelly executed. Accordingly, the time delay from the imaging request to actual irradiation can be shortened.

Additionally, the timing when the irradiation means is permitted to perform irradiation is determined from the initialization time of the image sensing means and the initialization time of grid movement (delay time until the grid moves to an appropriate target position), or the initialization time of the image sensing means, the irradiation delay time of the irradiation means, and the initialization time of grid movement. Therefore, imaging operation control for an imaging request and initialization of the image sensing element and/or grid movement can be parallelly executed. Accordingly, the time delay from the imaging request to actual irradiation can be shortened. Furthermore, since grid movement such as the grid position or speed can be controlled in consideration of the irradiation delay time corresponding to the irradiation means used for imaging, a satisfactory image without any grid stripe image formation on the object can be obtained.

Hence, according to the above embodiments, a satisfactory image can be obtained at a desired imaging timing.

For example, when the present invention is applied to radiation imaging, a satisfactory radiation image without any grid stripe image formation on the object can be provided, and any diagnostic error in image diagnosis can be reliably prevented.

The present invention is not limited to the above embodiments and various changes and modifications can be made within the spirit and scope of the present invention. Therefore, to apprise the public of the scope of the present invention, the following claims are made.

What is claimed is:

1. An imaging apparatus comprising:
   an image sensing unit adapted for sensing an electromagnetic wave image of a subject; and
   a controller adapted for generating a first signal for permitting an irradiating unit to irradiate an electromagnetic wave and a second signal for initializing said image sensing unit, so as to overlap a first period and a second period,
   wherein the first period is an interval between a timing when the first signal is outputted from said controller and a timing when the electromagnetic wave is outputted from said irradiating unit, and
   wherein the second period is an interval between a timing when the second signal is outputted from said controller and a timing when the initialization of said image sensing unit has been completed.

2. An apparatus according to claim 1, wherein said controller controls so that one of the first signal and the second signal starts after the other has started and before it has stopped.

3. An apparatus according to claim 1, wherein said image sensing unit has a photo-electric conversion device which outputs a signal in accordance with an electromagnetic wave and the second period is an interval between a timing when the second signal, for initializing said photo-electric conversion device, is outputted from said controller and a timing when the initialization of said photo-electric conversion device has been completed.

4. An apparatus according to claim 3, wherein the second period is an interval for a pre-discharge of said photo-electric conversion device.

5. An apparatus according to claim 1, wherein said image sensing unit has a grid which absorbs scattered rays from the subject, and said controller generates a third signal for driving said grid so as to overlap the first, the second and a third period, wherein the third period is an interval between a timing when the third signal is outputted from said controller and a timing when the initialization of said grid has been completed.

6. An apparatus according to claim 5, wherein the initialization of said grid is that a position and a moving speed of said grid should reach a target.

7. An apparatus according to claim 1, wherein said image sensing unit has a photo-electric conversion device which outputs a signal in accordance with an electromagnetic wave and a grid which absorbs scattered rays from the subject, and said controller generates a third signal for driving said grid so as to overlap the first, the second and a third period, wherein the third period is an interval between a timing when the third signal is outputted from said controller and a timing when the initialization of said grid has been completed.

8. An apparatus according to claim 1, wherein said controller generates the first signal so that an irradiation of the electromagnetic wave starts at a timing when a fourth period is elapsed after said controller has received a fourth signal which instructs a start of imaging, the fourth period being the longer one of the first and second period.

9. An apparatus according to claim 5, wherein said controller generates the first signal so that an irradiation of the electromagnetic wave starts at timing when a fourth period is elapsed after said controller has received a fourth signal which instructs a start of imaging, the fourth period being the longest one of the first, second and third period.

10. An imaging system comprising:
    an irradiating unit adapted for irradiating an electromagnetic wave;
    an image sensing unit adapted for sensing an electromagnetic wave image of a subject using the electromagnetic wave; and
    a controller adapted for generating a first signal for permitting said irradiating unit to irradiate the electromagnetic wave and a second signal for initializing said image sensing unit, so as to overlap a first period and a second period,
    wherein the first period is an interval between a timing when the first signal is outputted from said controller and a timing when the electromagnetic wave is outputted from said irradiating unit, and
    wherein the second period is an interval between a timing when the second signal is outputted from said controller and a timing when the initialization of said image sensing unit has been completed.

11. A method adapted to an imaging apparatus including an image sensing unit adapted for sensing an electromagnetic wave image of a subject, comprising a step of:

controlling a controller to generate a first signal for permitting an irradiating unit to irradiate an electromagnetic wave and a second signal for initializing the image sensing unit, so as to overlap a first period and a second period, wherein the first period is an interval between a timing when the first signal is outputted from the controller and a timing when the electromagnetic wave is outputted from the irradiating unit, and wherein the second period is an interval between a timing when the second signal is outputted from the controller and a timing when the initialization of the image sensing unit has been completed.

12. A method according to claim 11, wherein in said controlling step, one of the first signal and the second signal is started after the other has started and before it has stopped.

13. A method according to claim 11, wherein the image sensing unit has a photo-electric conversion device which outputs a signal in accordance with an electromagnetic wave and the second period is an interval between a timing when the second signal, for initializing the photo-electric conversion device, is outputted from the controller and a timing when the initialization of the photo-electric conversion device has been completed.

14. A method according to claim 13, wherein the second period is an interval for a pre-discharge of the photo-electric conversion device.

15. A method according to claim 11, wherein the image sensing unit has a grid which absorbs scattered rays from the subject, and said controlling step includes controlling the controller to generate a third signal for driving the grid so as to overlap the first, the second and a third period, wherein the third period is an interval between a timing when the third signal is outputted from the controller and a timing when an initialization of the grid has been completed.

16. A method according to claim 15, wherein the initialization of the grid is that a position and a moving speed of the grid should reach a target.

17. A method according to claim 11, wherein the image sensing unit has a photo-electric conversion device which outputs a signal in accordance with an electromagnetic wave and a grid which absorbs scattered rays from the subject, and said controlling step includes controlling the controller to generate a third signal for driving the grid so as to overlap the first, the second and a third period, wherein the third period is an interval between a timing when the third signal is outputted from the controller and a timing when an initialization of said grid has been completed.

18. A method according to claim 11, wherein in said controlling step, the first signal is generated so that an irradiation of the electromagnetic wave starts at a timing when a fourth period is elapsed after the controller has received a fourth signal which instructs a start of imaging, the fourth period being the longer one of the first and second period.

19. A method according to claim 15, wherein in said controlling step, the first signal is generated so that an irradiation of the electromagnetic wave starts at a timing when a fourth period is elapsed after the controller has received a fourth signal which instructs a start of imaging, the fourth period being the longest one of the first, second and third period.

20. A computer-readable storage medium which stores a program for executing a method adapted to an imaging apparatus including an image sensing unit adapted for sensing an electromagnetic wave image of a subject, the method comprising a step of:

controlling a controller to generate a first signal for permitting an irradiating unit to irradiate an electromagnetic wave and a second signal for initializing the image sensing unit, so as to overlap a first period and a second period, wherein the first period is an interval between a timing when the first signal is outputted from the controller and a timing when the electromagnetic wave is outputted from the irradiating unit, and wherein the second period is an interval between a timing when the second signal is outputted from the controller and a timing when the initialization of the image sensing unit has been completed.

21. An imaging apparatus comprising:

an irradiating unit for irradiating an electromagnetic wave:

a grid which is arranged in irradiating path of the electromagnetic wave;

a grid moving unit for moving said grid in the irradiating path;

an image sensing unit for converting the electromagnetic wave to image data, said image sensing unit having a plurality of image sensing elements;

a storage device for storing combinations of a first time interval which is a time interval between a timing when an irradiation permission signal is sent to said irradiating unit and a timing when an irradiation starts, a second time interval which is a time interval between a timing when said grid moving unit starts driving of said grid and a timing when said grid reaches a target position and a target speed, and a third time interval in which said image sensing unit is initialized, so that each of the combinations of the first time interval, the second time interval and the third time interval corresponds to each of a plurality of image sensing conditions;

an image sensing condition instructing device for inputting an image sensing condition; and a controller for controlling said irradiating unit, said grid moving unit and said image sensing unit, wherein, said controller selects a combination of the first time interval, the second time interval and the third time interval corresponding to the image sensing condition instructed by said image sensing condition instructing device, and controls so that a timing when said irradiating unit starts an irradiation, a timing when said grid reaches the target position and the target speed, and a timing when an initialization driving of said image sensing unit is completed coincide with each other, based an the selected combination.

22. An apparatus according to claim 21, wherein said controller transmits the irradiation permission signal, a driving start signal of said grid moving unit and a start signal of the initialization driving at a timing for coincidence of a timing when said irradiating unit starts an irradiation, a timing when said grid reaches the target position and the target speed, and a timing when an initialization driving of said image sensing unit is completed.

23. An apparatus according to claim 21, further comprising an image sensing instruction unit for inputting an image sensing request signal, wherein said controller controls so that a longest time in the first time interval, the second time interval and the third time interval corresponding to the image sensing condition instructed by said image sensing condition instructing device coincide with a time interval between a timing when the image sensing request signal is inputted and a timing when said irradiating unit starts irradiation.

24. An apparatus according to claim 21, wherein said controller controls to stop a moving control of said grid moving unit after an actual irradiation time is elapsed from the timing when said irradiating unit starts an irradiation, and to start reading of a signal from said image sensing unit after a predetermined time elapsed from the timing when the moving control has been stopped.

25. An apparatus according to claim 21, further comprising an electromagnetic wave detecting device for detecting an amount of the electromagnetic wave, wherein said controller controls to stop a moving control of said grid moving unit based on an output signal of said electromagnetic wave detecting device.

26. An imaging apparatus comprising:

an irradiating unit for irradiating an electromagnetic wave;

an image sensing unit for converting the electromagnetic wave to image data, said image sensing unit having a plurality of image sensing elements;

a storage device for storing combinations of a first time interval which is a time interval between a timing when an irradiation permission signal is sent to said irradiating unit and a timing when an irradiation starts, and a second time interval in which said image sensing unit is initialized, so that each of the combinations of the first time interval and the second time interval corresponds to each of a plurality of image sensing conditions;

an image sensing condition instructing device for inputting an image sensing condition: and a controller for controlling said irradiating unit and said image sensing unit, wherein, said controller selects a combination of the first time interval and the second time interval corresponding to the image sensing condition instructed by said image sensing condition instructing device, and controls so that a timing when said irradiating unit starts an irradiation and a timing when an initialization driving of said image sensing unit is completed coincide with each other, based on the selected combination.

27. An apparatus according to claim 26, wherein said controller transmits the irradiation permission signal and a start signal of the initialization driving at a timing for coincidence of a timing when said irradiating unit starts an irradiation and a timing when an initialization driving of said image sensing unit is completed.

28. An imaging apparatus comprising:

a grid which is arranged in irradiating path of the electromagnetic wave;

a grid moving unit for moving said grid in the irradiating path;

an image sensing unit for converting the electromagnetic wave to image data, said image sensing unit having a plurality of image sensing elements;

a storage device for storing combinations of a first time interval which is a time interval between a timing when said grid moving unit starts driving of said grid and a timing when said grid reaches a target position and target speed, and a second time interval in which said image sensing unit is initialized, so that each of the combinations of the first time interval and the second time interval corresponds to each of a plurality of image sensing conditions;

an image sensing condition instructing device for inputting an image sensing condition; and a controller for controlling said grid moving unit and said image sensing unit, wherein, said controller selects a combination of the first time interval and the second time interval corresponding to the image sensing condition instructed by said image sensing condition instructing device, and controls so that a timing when said grid reaches the target position and the target speed and a timing when an initialization driving of said image sensing unit is complete coincide with each other, based on the selected combination.

29. An apparatus according to claim 28, wherein said controller transmits a driving start signal of said grid moving unit and a start signal of the initialization driving at a timing for coincidence of a timing when said grid reaches the target position and the target speed and a timing when an initialization driving of said image sensing unit is completed.

* * * * *

UNITED STATES PATENT AND TRADEMARK OFFICE
CERTIFICATE OF CORRECTION

PATENT NO. : 6,782,077 B2
DATED : August 24, 2004
INVENTOR(S) : Akira Hirai

It is certified that error appears in the above-identified patent and that said Letters Patent is hereby corrected as shown below:

Column 5,
Line 67, please delete "185" and insert therefore -- 105 --

Column 9,
Line 3, please delete "*T*1-*T*xs-200 ms" and insert therefore -- *T*1-*Txs* = 200 ms --

Signed and Sealed this

Fifth Day of April, 2005

JON W. DUDAS
*Director of the United States Patent and Trademark Office*